(12) United States Patent
Prochazka et al.

(10) Patent No.: US 8,728,466 B2
(45) Date of Patent: May 20, 2014

(54) TREATING BURN INJURIES WITH REDUCED HYPERTROPHIC SCARRING

(75) Inventors: Vaclav Prochazka, Ostrava-Poruba (CZ); Hana Klosova, Studénka (CZ); Giannoula Lakka Klement, Boston, MA (US)

(73) Assignee: University Hospital Ostrava, Ostrava-Poruba (CZ)

( * ) Notice: Subject to any disclaimer, the term of this patent is extended or adjusted under 35 U.S.C. 154(b) by 73 days.

(21) Appl. No.: 13/302,866

(22) Filed: Nov. 22, 2011

(65) Prior Publication Data
US 2012/0156184 A1 Jun. 21, 2012

Related U.S. Application Data

(60) Provisional application No. 61/416,967, filed on Nov. 24, 2010.

(51) Int. Cl.
*A01N 63/00* (2006.01)
(52) U.S. Cl.
USPC ..... 424/93.72; 424/93.7; 424/530; 623/15.12
(58) Field of Classification Search
None
See application file for complete search history.

(56) References Cited

U.S. PATENT DOCUMENTS

2009/0042229 A1 2/2009 Folkman et al.

OTHER PUBLICATIONS

Ofodile et al. J Natl Med Assoc. May 1991; 83(5): 416-418.*
Pallua et al. Burns 36 ( 2 010 ) 4-8.*
Akeda et al., "Platelet-rich plasma (PRP) stimulates the extracellular matrix metabolism of porcine nucleus pulposus and anulus fibrosus cells cultured in alginate beads," *Spine*, 2006, 31(9):959-66.
Akingboye et al., "Application of autologous derived-platelet rich plasma gel in the treatment of chronic wound ulcer: diabetic foot ulcer," *J Extra-corpor Technol.*, 2010, 42(1):20-29.
Bottcher-Haberzeth et al., "Tissue engineering of skin," *Burns: J Int 'l Soc Burn Injuries*, 2010, 36(4):450-60.
Coetzee et al., "The use of autologous concentrated growth factors to promote syndesmosis fusion in the Agility total ankle replacement. A preliminary study," *Foot Ankle Int'l*, 2005, 26(10):840-46.
Crkvenjas et al., "Surgical treatment of electrical burns by local flap plastic surgery," *Acta chirurgiae plasticae*, 2005, 47(1):10-12.
Draaijers et al., "Colour evaluation in scars: tristimulus colorimeter, narrow-band simple reflectance meter or subjective evaluation?" *Burns: J Int'l Soc Burn Injuries*, 2004, 30(2):103-7.
Elman et al., "The 5-D itch scale: a new measure of pruritus," *Br J Dermatol.*, 2010, 162(3):587-93.
Gardner et al., "The efficacy of autologous platelet gel in pain control and blood loss in total knee arthroplasty. An analysis of the haemoglobin, narcotic requirement and range of motion," *Int 'l Orthopaedics* 2007, 31(3):309-13.

Gunaydin et al., "Clinical impact and biomaterial evaluation of autologous platelet gel in cardiac surgery," *Perfusion*, 2008, 23(3):179-86.
Hermann et al., "Concentration of bone marrow total nucleated cells by a point-of-care device provides a high yield and preserves their functional activity," *Cell Transplantation*, 2008, 16(10):1059-69.
Italiano et al., "Angiogenesis is regulated by a novel mechanism: pro- and antiangiogenic proteins are organized into separate platelet alpha granules and differentially released," *Blood*, 2008, 111(3):1227-33.
Kabes et al., "Further validation of the nonverbal pain scale in intensive care patients," *Critical Care Nurse*, 2009, 29(1):59-66.
Kachel et al., "Treatment of deep sternal wound infections after coronary artery bypass grafting by means of injection of platelet gel: an evolving technology," *J Thoracic and Cardiovascular Surg.*, 2010, 139(6):e118-20.
Khalafi et al., "Topical application of autologous blood products during surgical closure following a coronary artery bypass graft," *Eur J CardioThorac Surg.*, 2008, 34(2):360-64.
Klement et al., "Platelets actively sequester angiogenesis regulators," *Blood*, 2009, 113(12):2835-42.
Kloppenberg et al., "Perfusion of burn wounds assessed by Laser Doppler Imaging is related to burn depth and healing time," *Burns: J Int'l Soc Burn Injuries*, 2001, 27(4):359-63.
Langer et al., "Adherent platelets recruit and induce differentiation of murine embryonic endothelial progenitor cells to mature endothelial cells in vitro," *Circ Res.*, 2006, 98(2):e2-10.
Lindemann et al., "Platelets, inflammation and atherosclerosis," *J Thromb. Haemostasis*, 2007, 5 Suppl 1:203-11.
Ma et al., "Proteinase-activated receptors 1 and 4 counter-regulate endostatin and VEGF release from human platelets," *PNAS*, 2005, 102(1):216-20.
Martinez-Zapata et al., "Efficacy and safety of the use of autologous plasma rich in platelets for tissue regeneration: a systematic review," *Transfusion*, 2009, 49(1):44-56.
Mazzucco et al., "Platelet-rich plasma and platelet gel preparation using Platletex®," *Vox Sanguinis*, 2008, 94(3):202-8.
Mazzucco et al., "The use of autologous platelet gel to treat difficult-to-heal wounds: a pilot study," *Transfusion*, 2004, 44(7):1013-18.
Morizaki et al., "The effects of platelet-rich plasma on bone marrow stromal cell transplants for tendon healing in vitro," *J Hand Surg.*, 2010, 35(11):1833-41.
Orenstein et al., "Treatment of deep sternal wound infections post-open heart surgery by application of activated macrophage suspension," *Wound Rep Reg.*, 2005, 13:237-242.
Pietramaggiori et al., "Tumors stimulate platelet delivery of angiogenic factors in vivo: an unexpected benefit," *Am J Pathol.*, 2008, 173(6):1609-16.
Pintucci et al., "Trophic effects of platelets on cultured endothelial cells are mediated by platelet-associated fibroblast growth factor-2 (FGF-2) and vascular endothelial growth factor (VEGF)," *Thromb Haemost*, 2002, 88(5):834-42.
Prochazka et al., "Cell therapy, a new standard in management of chronic critical limb ischemia and foot ulcer," *Cell Transplantation*, 2010, 19(11):1413-24.

(Continued)

Primary Examiner — Blaine Lankford
(74) *Attorney, Agent, or Firm* — Fish & Richardson P.C.

(57) ABSTRACT

This document provides methods and materials involved in treating burn injuries. For example, methods and materials for using skin grafts (e.g., autologous skin grafts) treated with an autologous platelet concentrate and autologous thrombin to treat burn injuries (e.g., deep skin burn injuries) are provided.

6 Claims, 10 Drawing Sheets

(56) References Cited

OTHER PUBLICATIONS

Stellos et al., "Platelet aggregates-induced human $CD34^+$ progenitor cell proliferation and differentiation to macrophages and foam cells is mediated by stromal cell derived factor 1 in vitro," *Seminars Thromb Hemost.*, 2010, 36(2):139-45.

Xu et al., "Application of a partial-thickness human ex vivo skin culture model in cutaneous wound healing study," *Laboratory Investigation*, 2012, 92(4):584-99.

Xu et al., "Tissue architecture and function: dynamic reciprocity via extra- and intra-cellular matrices," *Cancer Metastasis Reviews*, 2009, 28(1-2):167-76.

* cited by examiner

TREATING BURN INJURIES WITH REDUCED HYPERTROPHIC SCARRING

CROSS-REFERENCE TO RELATED APPLICATIONS

This application claims the benefit of U.S. Provisional Application Ser. No. 61/416,967, filed Nov. 24, 2010. The disclosure of the prior application is considered part of (and is incorporated by reference in) the disclosure of this application.

BACKGROUND

1. Technical Field

This document relates to methods and materials involved in treating burn injuries. For example, this document provides methods and materials for using skin grafts (e.g., autologous skin grafts) treatment with an autologous platelet rich plasma (PRP) concentrate and human autologous thrombin for the treatment of deep burn injuries.

2. Background Information

Deep skin burns injuries, especially extensive deep burns (i.e., third-degree and deep second-degree burns) extending for example on the face, neck, hands, feet, genitalia, and perineum remain one the most challenging problems for modern medicine. Deep burns are very painful, and there are a many complications associated with deep burns. Extensive deep burn injuries can be associated with difficult and complicated clinical courses (e.g., shock, infection, multiple organ dysfunction syndrome (MODS), electrolyte imbalance, and respiratory distress) with high morbidity and mortality rates. Therapeutic results sometimes are unacceptable due to functional and cosmetic deficits causing severe psychological and emotional distress, particularly due to scarring and physical deformity (e.g., hypertrophic scars, joint contractures, peripheral neuropathy, psychiatric and psychological diseases, and thermoregulation disorders). Consequently, the quality of life after severe burn injury is markedly decreased.

SUMMARY

This document provides methods and materials involved in treating deep burn injuries. For example, this document provides methods and materials for using skin grafts (e.g., autologous skin grafts) treatment with an autologous platelets rich plasma (PRP) concentrate and thrombin (e.g., human autologous thrombin (HAT)) to treat burn injuries (e.g., deep skin burn injuries).

As described herein, a skin graft can be exposed to an autologous PRP concentrate with HAT, such that application of the skin graft to a patient's burn site results in improved healing characteristics. For example, application of such skin grafts can result in rapid healing with no scarring (e.g., hypertrophic scaring), healing with rapidly reduced pain, and/or healing with reduced risk of infection. Healed skin is very smooth, and elasticity is very similar to normal skin. In some cases, no additional plastic surgery or re-operation is necessary. In some cases, patients treated as described herein can experience in hospital stays that are significantly shorter than other types of treatments. Having the ability to treat burn victims in a manner that results in less scarring, less pain, and/or less risk of infection is beneficial to both patients and clinicians. For example, a clinician knowing that the methods and materials provided herein can be used to treat burned tissue in a manner that can reduce pain and can result in no scarring can confidently operate on a larger burn site.

In general, one aspect of this document features a method for treating a second or third degree skin burn of a mammal. The method comprises, or consists essentially of, applying a skin graft, platelet concentrate, and thrombin preparation to at least a portion of the burn site of the second or third degree skin burn. The mammal can be a human. The skin graft can be an autologous meshed skin graft. The platelet concentrate can be an autologous platelet concentrate. The thrombin preparation can be a human autologous thrombin preparation. The skin graft can be exposed to the platelet concentrate and the thrombin after applying the skin graft to the burn site.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features, objects, and advantages of the invention will be apparent from the description and drawings, and from the claims.

DETAILED DESCRIPTION

Figure 1:
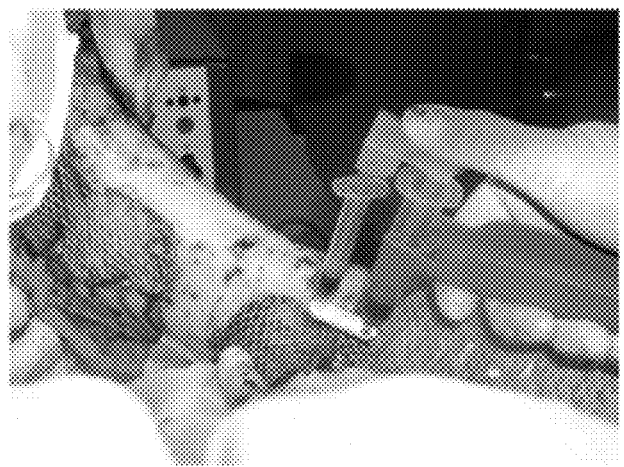
FIG. 1 is a photograph of a SmartJet® Liquid and Spray Delivery applicator (Harvest Technologies Corp., 40 Grissom Road, Plymouth, Mass. 02360), which is commercially available and is used to apply autologous platelet concentrate (APC) and human autologous thrombin to a skin graft.
Figure 2A:
FIGS. 2A, 2B, 3A, and 3B are photographs of a burn wound before (A) and 30 days after (B) treatment with DE graft plus APC exposed to human autologous thrombin. No hypertrophic scars can be detected.
Figure 2B:
Figure 3A:
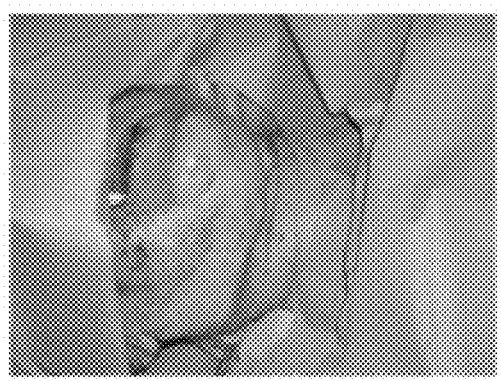
Figure 3B:
Figure 4:
FIG. 4 contains photographs of a burn wound 60 days after treatment without APC and not exposed to human autologous thrombin. Significant hypertrophic scarring is visible.

This document provides methods and materials involved in treating burn injuries. For example, this document provides methods and materials for using skin grafts (e.g., autologous skin grafts) treated with platelet rich plasma (PRP) or an autologous platelet concentrate (APC) in combination with thrombin (e.g., human autologous thrombin) to treat burn injuries (e.g., deep skin burn injuries).

As described herein, a skin graft can be exposed to a platelet concentrate that is exposed to thrombin (e.g., human autologous thrombin) such that application of the skin graft to a patient's burn site results in improved healing characteristics. Appropriate autologous skin graft can be used including, without limitation, a meshed skin graft. Once obtained, a skin graft can be contacted with PRP or APC that has been exposed to thrombin (e.g., human autologous thrombin).

Any appropriate method can be used to obtain a platelet rich plasma concentrate including, centrifugation methods by gradient density centrifuge. Platelet concentrate can be maintained in the presence of an anticoagulant such as anticoagulant citrate dextrose solution Formula A (ACD-A).

Any appropriate method can be used to obtain thrombin (e.g., human autologous thrombin). For example, standard thrombin isolation methods such as those involving the use of commercially available kits (e.g., from APC-Harvest Technologies) can be used to obtain human autologous thrombin. In some cases, thrombin can be obtained commercially.

In some cases, a skin graft can be placed in contact with a burn wound prior to treating the graft and wound with a platelet concentrate (e.g., APC) exposed to thrombin (e.g., human autologous thrombin). In some cases, a skin graft can be exposed to a platelet concentrate (e.g., APC) and exposed to thrombin (e.g., human autologous thrombin) prior to being placed in contact with a burn wound. For example, in difficult operating positions, a skin graft can be exposed to PRP or ACP and exposed to thrombin (e.g., human autologous thrombin) prior to being placed in contact with a burn wound.

In some cases, a platelet concentrate (e.g., APC) and thrombin preparation can be applied to a skin graft at the same time or at substantially the same time. In some cases, a platelet concentrate (e.g., APC) can be exposed to thrombin (e.g., human autologous thrombin) after a skin graft is contacted with the platelet concentrate.

The invention will be further described in the following examples, which do not limit the scope of the invention described in the claims.

EXAMPLES

Example 1

Autologous Platelets Concentrate and Human Autologous Thrombin for the Treatment of Deep Burns Trauma 17 patients (9 men, 8 women) were included in this study. The mean age was 56 years (range 33-83). Each patient signed informed consent with surgery treatment (i.e., surgical excision of devitalised tissue, dermoepidermal transplantation, and local transplantation of autologous platelet concentrate (APC) and autologous thrombin). The mean extent of deep burned skin with local transplantation of APC was 3% TBSA—Total Body Surface Area (range from 1.5% to 4% TBSA). The mechanism of burn injury was hot water, a flame, glowing liquid metal, or an explosion of gas. Seven patients were smokers, and 10 patients were non-smokers. One patient had diabetes mellitus type I and was on insulin therapy.

The inclusive criteria required each patient to be an adult patient (over 18 years of age) with deep burn injury indicated for surgery treatment (e.g., surgical excisions of devitalised tissue followed by dermoepidermal transplantation) and to have signed the patient's informed consent form.

The exclusive criteria included inborn trombocytopaenia, haematological malignities, chronical renal failure (which may result in a deficiency of effective platelets), and unsigned patient's informed consent.

Methodology

Figure 5:
FIG. 5 is a photograph of a skin grafting procedure.

The surgical treatment was indicated on the base of the depth of burns. Sixteen patients were indicated to necrectomy primarily, and one patient underwent surgical abrasion as for secondary disrepair of spontaneously healing burns on the face. The treatment involved dermoepidermal meshed graft transplantation with local transplantation of autologous platelet concentrate (APC) plus human autologous thrombin in an effort to achieve a higher speed and quality of healing, to achieve the higher quality of scarring processes, and to reduce the risk of hypertrophic scarring. The skin dermoepidermal grafts (e.g., split thickness skin grafts) were taken by electric dermatome from, for example, the donor's thighs (FIG. 5).

Figure 6:
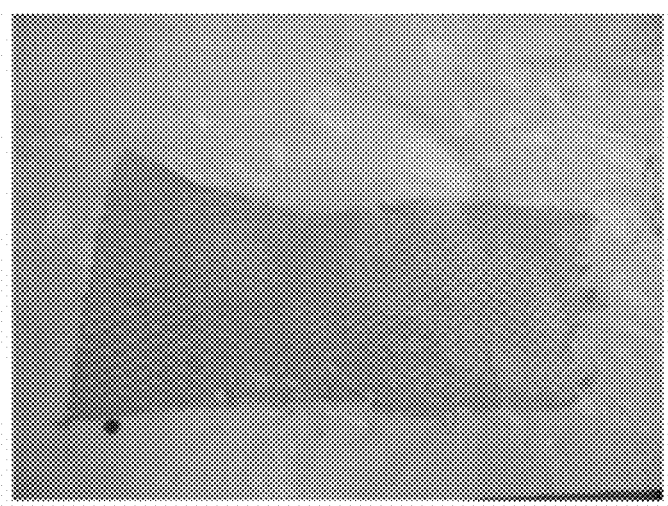
FIG. 6 is a photograph of a meshed autologous skin graft.

The skin grafts were meshed before transplantation with expansion 1:1.5 or 1:2 in 15 patients (FIG. 6). In one case, grafts were only manually perforated by scalpel in order to achieve good cosmetic results since the recipient area was the face.

Figure 7:
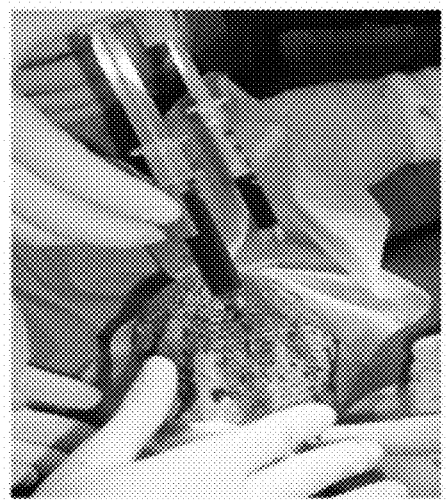
FIG. 7 is a photograph of the application of PRP plus human autologous thrombin.

After dermoepidermal transplantation, the direct local transplantation of APC to the areas with skin grafts followed. The APC was applied simultaneously with human autologous thrombin, by means of a SmartJet® applicator (HarvestTechnologies Corp., 40 Grissom Road, Plymouth, Mass. 02360), as an agent for activating platelets (FIG. 7).

Figure 8:
FIG. 8 is a photograph of a Surfasoft dressing after application of a DE graft treated with APC and human autologous thrombin.

After application, an incubation of about 20 seconds was used to allow the APC to gel and fix the skin graft. Then, the transplanted areas were covered with Surfasoft® foil dressing (TAUREON Laan van Zuid Hoorn 61 2289 DC RIJSWIJK ZH Nederland). The margins of the foil dressing were fixated using disposable skin staplers to protect the skin grafts and to prevent their dislocation. Gauze wetted in a saline solution was applied as a subsequent layer followed by a layer of dry gauze. The dressing was covered with an elastic roller bandage (FIG. 8).

Surfasoft® is an inert, neutral wound contact dressing material that can be manufactured from a monofilament woven polyamide thread, which allows drainage over 45 percent of its surface. Its design is strong, flexible, and causes minimum adherence and friction to the skin grafts. This allows manipulation of anatomically difficult areas. The smooth surface of the material also means that bacteria do not easy adhere to it. Transparency of the Surfasoft® allows wound inspection throughout the treatment. Surfasoft® is well accepted by the wound tissue.

Preparation of the APC

The Harvest SmartPRep2 Platelet Concentrate System ((HarvestTechnologies Corp., 40 Grissom Road, Plymouth, Mass. 02360) was used to prepare the APC and autologous thrombin. The procedure was performed in the operation room under aseptic conditions. The patient's peripheral venous blood was taken using standard blood drawing techniques simultaneously with the start of the operation. Blood was drawn most frequently from the antecubital or cephalic vein or from any other vein that was reachable. Firstly, 10 mL of venous blood was taken to prepare a human autologous thrombin preparation and allowed to stand for about 45 minutes. This results in about 5 mL of human autologous thrombin. After 30 minutes, 60 mL of venous blood was taken to prepare the APC. The venous blood together with and anticoagulant (e.g., anticoagulant citrate dextrose solution Formula A (ACDA)) was placed in a separator and subjected to gradient density centrifugation (e.g., 14 minutes at 1000 rpm). This technique fully complies with the modern demands of current medical and clinical use: (1) the gain of sufficient amount of autologous thrombocytes by separation from the venous blood, and (2) easy, rapid, and safe way of blood draw and its separation without multiple manipulations of blood bags or tests tubes. After finishing the process of centrifugation, 10 mL of APC was obtained along with plasma poor proteins as an accessory product. Thus, when drawing 60 mL of venous blood, 10 mL of APC was obtained, which can cover up to 4 percent of the total body skin surface. The next step involved the direct application of the APC and the human autologous thrombin by means of the SmartJet® applicator ((HarvestTechnologies Corp 40 Grissom Road, Plymouth, Mass. 02360 Phone (508)732-7500 Fax (508)732-0400 to the areas with skin grafts.

Haematological Analysis of APC

Samples of APC and the PPP platelet poor plasma were analyzed for count and shape of platelets and levels of growth factors (i.e., Platelet Derived Growth Factor (PDGF), Transforming Growth Factor Beta 1 (TGF-beta1), Epithelial Growth Factor (EGF), and Vascular Endothelial Growth Factor (VEGF)) (Table 1).

TABLE 1

| ID | PDGF [pg/mL] | VEGF [pg/mL] |
|---|---|---|
| 1 | 100.35 | 37.43 |
| 3 | 103.46 | 72.18 |
| 7 | 258.90 | 64.90 |
| 8 | 145.185 | 82.91 |

The haematological analysis of APC samples was performed for 17 patients. The count of platelets was increased above baseline from 2.75× to 5.05× (mean 3.07±0.149 SEM) (Table 2).

TABLE 2

Increase of the thrombocytes concentration on APC when compared to venous blood. Analysis - PLT count

| ID | Platelet Rich Plasma PRP - PLT count | Peripheral Blood - PLT count | Platelet Poor Plasma - PLT count | Increase of baseline PRP/PB |
|---|---|---|---|---|
| 1 | 1391 | 357 | 63 | 3.9 |
| 2 | 853 | 310 | 59 | 2.8 |
| 3 | 857 | 301 | 43 | 2.8 |
| 4 |  | 527 |  |  |
| 5 | 1402 | 407 | 75 | 3.4 |
| 6 | 1726 | 476 | 114 | 3.6 |
| 7 | 1050 | 347 | 45 | 3 |
| 8 | 610 | 271 | 37 | 2.3 |
| 9 | 809 | 346 | 22 | 2.3 |
| 10 | 1004 | 382 | 100 | 2.6 |
| 11 | 809 | 345 | 32 | 2.3 |
| 12 | 920 | 337 | 52 | 2.7 |
| 13 | 1178 | 359 | 94 | 3.3 |
| 14 | 1264 | 336 | 57 | 3.8 |
| 15 | 1090 | 290 | 61 | 3.8 |
| 16 | 876 | 248 | 24 | 3.5 |
| Mean | 1060 | 352 | 58.5 | 3.07 |
| St. Dev. | 292 | 71.3 | 27.4 | 0.578 |
| S.E.M. | 75.5 | 17.8 | 7.08 | 0.149 |
| Count | 15 | 16 | 15 | 15 |
| median | 1004 | 345.5 | 57 | 3 |
| modus | 809 |  | 63 | 2.3 |
| MAX | 1726 | 527 | 114 | 3.9 |
| MIN | 610 | 248 | 22 | 2.3 |
| Variation | 1116 | 279 | 92 | 1.6 |
| Variation coefficient | 27.54716981 | 20.25568182 | 46.83760684 | 18.82736156 |

Histolopathological Analysis

Figure 9:
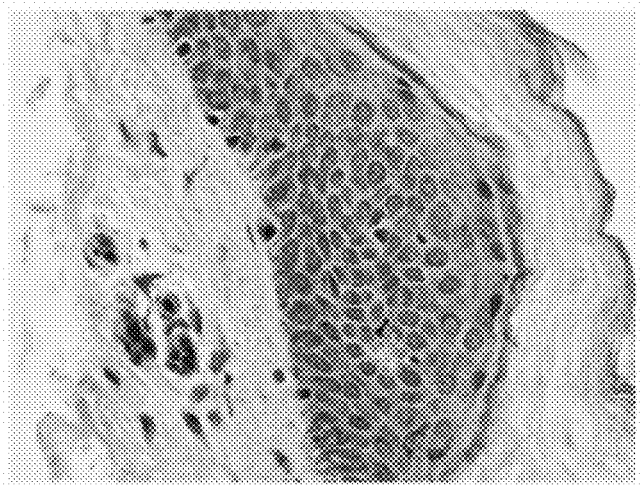
FIG. 9 is a photograph of an immunohistology analysis with an anti-PDGF antibody of DE Graft after application of PRP and human autologous thrombin. Magnification=400 times.
Figure 10:
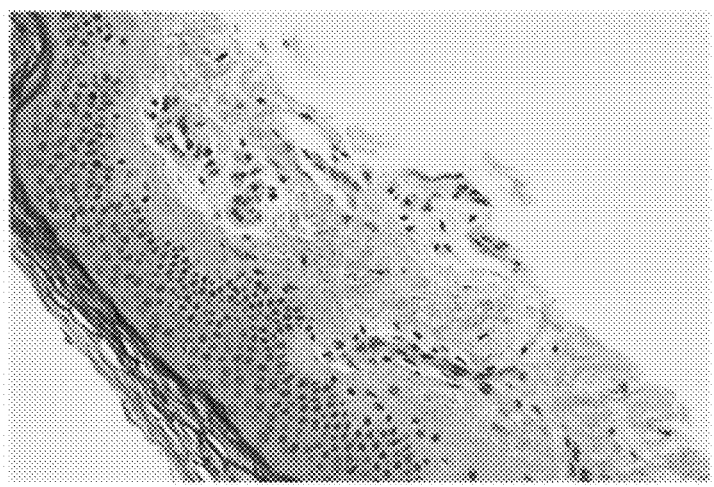
FIG. 10 is a photograph of an histology analysis of a DE Graft after application PRP and human autologous thrombin. Coloration=hematoxyline-eosin. Magnification=200 times.

In all patients, samples of necrotic tissue, healthy skin, and DE graft (Dermo-Epidermal Graft) with APC was screened to verify the presence of viable platelets and to detect growth factors (e.g., PDGF) released from platelets (FIGS. 9 and 10).

Postoperative Course

The first redressing was performed the second day after operation. Redressing was performed every other day after the first redressing in all patients. The vitality of skin grafts and the degree of epithelization were carefully observed during the course of every redressing by clinical visual and tactile examination and by digital photo-documentation.

During the postoperative course, non-complicated and full healing of all transplanted areas was observed in 16 patients. One patient with unstable diabetes mellitus type I (on insulin therapy) experienced complications after transplantation of 3.5% TBSA had bilaterally on the heals small residual areas, where skin grafts unattached (on each heal area about 1-2 cm$^2$). In these areas, a conservative treatment was used such that the patient underwent redressing twice a week. The complete healing on the heals was achieved on the 67th day for the left heal, and on the 123th day for the right heal. During all this time despite careful monitoring of glycaemia, the proper stabilization of diabetes was not achieved.

One patient, a woman after transplantation of 4% TBSA (Total Body Surface Area) on the back, had the majority of transplanted areas completely healed on the 10th post-operative day. On the several small areas between margins of skin grafts, where a small amount of dislocation of skin grafts occurred (about 0.75% TBSA), the healing was realized by epithelization from margins of skin grafts and was totally completed on the 28th day after operation. All areas after transplantation with APC visually exhibited a high quality of healing. By the 4th day after transplantation, the epithelization was very advanced. By the 6-7th day, epithelization of a majority of the transplanted areas was observed. By the 8th day after operation, one started to see the complete healing of a majority of the skin grafted areas. Also, very high quality of healing with reduced hypertrophic scarring was observed. The scars were judged using the Vancouver Scar Scale at 1 month, 3 months, and 6 months after transplantation (Table 3).

TABLE 3

Quality of healing process at one month follow-up.

| ID: | Days post-surgery | Pigmentation | Scar elasticity | Scar height | Vancouver Score |
|---|---|---|---|---|---|
| 1 | 31 | 0 | 1 | 0 | 2 |
| 2 | 33 | 0 | 1 | 0 | 3 |
| 3 | 32 | 0 | 1 | 0 | 2 |
| 4 | 30 | 0 | 1 | 0 | 2 |
| 5 | 32 | 1 | 1 | 1 | 3 |
| 6 | 29 | 2 | 1 | 0 | 4 |
| 7 | 33 | 2 | 1 | 1 | 5 |
| 8 | 29 | 0 | 1 | 0 | 3 |
| 9 | 29 | 0 | 1 | 0 | 2 |
| 10 | 28 | 0 | 3 | 0 | 4 |
| 11 | 33 | 2 | 1 | 0 | 4 |
| 12 | 32 | 2 | 1 | 0 | 5 |
| 13 | 32 | 0 | 2 | 1 | 4 |
| 14 | 30 | 1 | 1 | 1 | 3 |
| 15 | 27 | 0 | 1 | 1 | 2 |
| 16 | 32 | 0 | 1 | 0 | 2 |
| 17 | — | — | — | — | — |
| 18 | — | — | — | — | — |
| Mean | | 0.63 | 1.19 | 0.27 | 3.13 |
| St. Dev. | | 0.89 | 0.54 | 0.46 | 1.09 |
| Count | | 16 | 16 | 16 | 16 |
| Median | | 0 | 1 | 0 | 3 |
| Modus | | 0 | 1 | 0 | 2 |
| Min | | 0 | 1 | 0 | 2 |
| Max | | 2 | 3 | 1 | 5 |

At one month after transplantation of APC with human autologous thrombin, three patients' scars were as level as the surrounding healthy skin. One patient has scarring that was 1 mm about the surrounding healthy skin. In all 17 patients, the pliability of scars was supple (i.e., scars were flexible with minimal resistance). With respect to vascularity of scars, in four patients, scars were pink. In one patient, the color of scars was normal (i.e., closely resembling the color of the surrounding healthy skin. The pigmentation of scars was normal in two patients. Hypopigmentation was observed in nine patients, and mixed pigmentation was observed in one patient. The mean count of VSS was 3 points (range from 2 points to 4 points). No symptoms of hypertrophic scarring were observed in any of the patients, and every scar was cosmetically and functionally fully sufficient and highly favorable.

At three months after transplantation, scars were evaluated for three patients. One patient could not be evaluated due to the patient's non-compliance (e.g., non-participation on clinic examinations during out-patient course), and two patients had less than three months after operation. At three months after operation, scars were observed to be level with the surrounding healthy skin, were found to have sporadic, small regions of hypopigmentation, and were supple. In two patients, normal vascularity of scars was observed. In one patient, particularly pink and particularly normal vascularity scars were observed. The mean count of VSS was 3.13±1.09 points (range from 2 points to 5 points). Again, no symptoms of hypertrophic scarring were observed in any of the patients and every scar was cosmetically and functionally fully sufficient and highly favorable.

At six months after transplantation, scars were evaluated for two patients. Scars were in both cases level with the surrounding healthy skin, exhibited normal vascularity, were supple, and exhibited mixed pigmentation. In both cases, the total count of VSS was 3 points.

No complications of healing relate to the use of APC exposed to human autologous thrombin were observed in any patient. Post-operative infectious complications of healing or rejection of skin graft were not observed in any patient.

The results provided herein demonstrate that skin grafts (e.g., meshed autologous skin grafts) treated with APC exposed to thrombin (e.g., human autologous thrombin) can be used to accelerate healing of burn wounds and can result in an improved quality of healing. For example, burn wounds treated as described herein can exhibit reduced hypertrophic scarring, thereby requiring less reconstructive operations during the finally phase of burn injury (e.g., the phase of rehabilitation and reconstruction). Burn wounds treated as described herein can exhibit highly advanced epithelisation by the $4^{th}$ post-operative day and nearly complete epithelisation by the $6^{th}$ day after operation. Using the methods and materials described herein, the majority of a meshed skin graft can be completely healed by the $6^{th}$ to $8^{th}$ day after transplantation.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method for treating a second or third degree skin burn of a mammal with reduced risk of hypertrophic scarring, wherein said method comprises applying a skin graft, platelet rich plasma, and a thrombin preparation to at least a portion of the burn site of said second or third degree skin burn, and wherein said portion of said burn site heals with no visible hypertrophic scarring.

2. The method of claim 1, wherein said mammal is a human.

3. The method of claim 1, wherein said skin graft is an autologous meshed skin graft.

4. The method of claim 1, wherein said platelet rich plasma is autologous platelet rich plasma.

5. The method of claim 1, wherein said thrombin preparation is a human autologous thrombin preparation.

6. The method of claim 1, wherein said skin graft is exposed to said platelet rich plasma and said thrombin after applying said skin graft to said burn site.

* * * * *